(12) United States Patent
Keitel et al.

(10) Patent No.: US 11,058,868 B2
(45) Date of Patent: Jul. 13, 2021

(54) MANUFACTURING METHOD FOR A MICROLEAD

(71) Applicants: Heraeus Deutschland GmbH & Co. KG, Hanau (DE); Heraeus Medical Components LLC, St. Paul, MN (US)

(72) Inventors: Oliver Keitel, Aschaffenburg (DE); Markus Jung, Hanau (DE); Mark A. Hjelle, White Bear Lake, MN (US); Larry Lark, Saint Paul, MN (US)

(73) Assignees: Heraeus Deutschland GmbH & Co. KG, Hanau (DE); Heraeus Medical Components LLC, St. Paul, MN (US)

( * ) Notice: Subject to any disclaimer, the term of this patent is extended or adjusted under 35 U.S.C. 154(b) by 22 days.

(21) Appl. No.: 16/358,115

(22) Filed: Mar. 19, 2019

(65) Prior Publication Data

US 2019/0290898 A1 Sep. 26, 2019

(30) Foreign Application Priority Data

Mar. 23, 2018 (EP) .................................... 18163672

(51) Int. Cl.
| | |
|---|---|
| *A61N 1/05* | (2006.01) |
| *A61N 1/36* | (2006.01) |
| *A61N 1/362* | (2006.01) |
| *B29C 65/66* | (2006.01) |
| *B29L 31/34* | (2006.01) |

(52) U.S. Cl.
CPC .............. *A61N 1/05* (2013.01); *A61N 1/362* (2013.01); *A61N 1/3605* (2013.01); *A61B 2562/028* (2013.01); *A61B 2562/125* (2013.01); *B29C 65/665* (2013.01); *B29L 2031/34* (2013.01)

(58) Field of Classification Search
None
See application file for complete search history.

(56) References Cited

U.S. PATENT DOCUMENTS

| | | | |
|---|---|---|---|
| 6,071,281 A | 6/2000 | Burnside et al. | |
| 8,533,944 B2* | 9/2013 | Swanson ............... | A61N 1/0553 29/857 |
| 9,079,018 B2* | 7/2015 | Olsen .................... | A61N 1/0553 |
| 2003/0093072 A1 | 5/2003 | Friedman | |
| 2011/0106074 A1 | 5/2011 | Kunis et al. | |

(Continued)

FOREIGN PATENT DOCUMENTS

EP 0964720 12/1999

*Primary Examiner* — Brian T Gedeon
(74) *Attorney, Agent, or Firm* — Dicke, Billig & Czaja, PLLC

(57) ABSTRACT

One aspect is a manufacturing method including providing at least a first electrically conductive wire with an electrical insulation and a second electrically conductive wire with an electrical insulation, providing a first and a second ring electrode surrounding the wires, electrically connecting the first ring electrode with the first wire and the second ring electrode with the second wire, bundling the ring electrodes and the wires by means of a first sheath surrounding the ring electrodes and the wires to obtain a first ring electrode component, providing a second ring electrode component, bundling the ring electrode components by means of a second sheath surrounding the ring electrode components, and partially removing the first and the second sheaths from the ring electrodes to expose ring electrode portions.

15 Claims, 3 Drawing Sheets

(56) References Cited

U.S. PATENT DOCUMENTS

| | | |
|---|---|---|
| 2011/0137382 A1 | 6/2011 | Swanson |
| 2011/0166569 A1 | 7/2011 | Whayne et al. |
| 2013/0338745 A1 | 12/2013 | Ollivier et al. |
| 2014/0107455 A1 | 4/2014 | Régnier et al. |
| 2014/0296951 A1 | 10/2014 | Vetter et al. |
| 2016/0073960 A1 | 3/2016 | Jung et al. |
| 2016/0235967 A1 | 8/2016 | Shan et al. |
| 2019/0021620 A1* | 1/2019 | Olson .................. A61N 1/056 |

* cited by examiner

MANUFACTURING METHOD FOR A MICROLEAD

CROSS-REFERENCE TO RELATED APPLICATION

This Utility Patent Application claims priority to Application No. EP 18 163 672.1 filed on Mar. 23, 2018, which is incorporated herein by reference.

TECHNICAL FIELD

One aspect relates to a manufacturing method for a microlead, the microlead, a microlead system including such microlead and a use of such microlead or microlead system.

BACKGROUND

US2013338745 A1 relates to a multipolar lead for implantation in a venous, arterial, or lymphatic network, and for use with an electric stimulation or detection device. The multipolar lead includes at least two microcables, each having a central conductor for connection to the electric stimulation or detection device. The multipolar lead further includes a first ring having at least two lumens, each sized to receive a microcable of the at least two microcables, wherein one of the at least two lumens is a connection lumen which receives a first microcable of the at least two microcables. The ring further includes a connection element movable into the connection lumen to pierce a sheath of the first microcable and to press into the central conductor of the first microcable received by the connection lumen, electrically connecting at least a portion of the first ring to the central conductor.

The structure and manufacture of such device is rather complicated. There may be a need to provide an improved and easier and/or more flexible manufacturing method for a microlead.

SUMMARY

It should be noted that the aspects of the invention described in the following apply also to the manufacturing method for a microlead, the microlead, the microlead system including such microlead and the use of such microlead or microlead system.

According to one embodiment, a manufacturing method for a microlead is presented. The manufacturing method includes the following:

a) providing at least a first electrically conductive wire including an electrical insulation and a second electrically conductive wire including an electrical insulation, b) providing a first and a second ring electrode surrounding the wires at least partially, c) electrically connecting the first ring electrode with the first wire and the second ring electrode with the second wire, d) bundling the ring electrodes and the wires by means of a first sheath surrounding the ring electrodes and the wires at least partially to obtain a first ring electrode component, e) providing a second ring electrode component, f) bundling the ring electrode components by means of a second sheath surrounding the ring electrode components at least partially, and g) partially removing the first and the second sheaths from the ring electrodes to expose ring electrode portions.

This manufacturing method for a microlead is less complex than conventional manufacturing methods. For example, the present manufacturing method is elegant and flexible and provides microleads, which are more reliable and long-term stable than microleads manufactured according to conventional manufacturing methods.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1A:
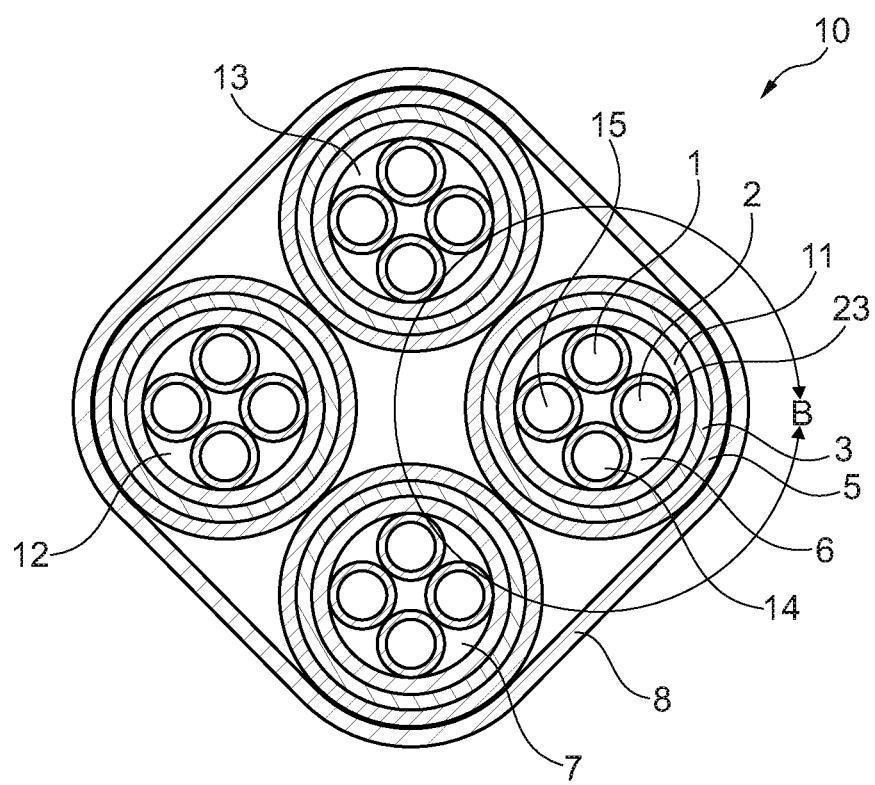
FIGS. 1a-1c illustrate schematically and exemplarily cross-sections of a microlead according to one embodiment, in FIG. 1a), a detail view of one part of the microlead in FIG. 1b) and a side view of the microlead in FIG. 1c)

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

An improved microlead can be manufactured, which is very small with respect to its diameter to avoid injuries of a venous, arterial, or lymphatic network, in which it is to be inserted. The diameter of a microlead manufactured according to the present manufacturing method can be below or equal to 1.2 mm and in one embodiment below or equal to 1 mm. It can also be in the range of 20 to 1000 µm and in one embodiment between 100 and 400 µm.

The present manufacturing method allows manufacturing such small microleads with still a high number of electrodes and/or exposed electrode portions. The electrodes and/or the exposed electrode portions may still have large electrode surfaces, which allow using less current densities, which again avoid injuries of the venous, arterial, or lymphatic network.

The present manufacturing method further allows manufacturing a microlead with an improved corrosion resistance when compared to a microlead manufactured by a conventional thin-film process. Further, various shapes and sizes of ring electrodes and exposed ring electrode portions can be provided.

An electrically conductive wire with an electrical insulation can be understood in that the wire is electrically conductive in its longitudinal direction and is electrically insulated in a direction perpendicular to its longitudinal direction. In an example, the electrical insulation of the wire is a coating around the electrically conductive wire. A thickness of the electrical insulation of the wire may be between 3 and 150 µm and in one embodiment between 5 and 40 µm.

The wording "providing an electrically conductive wire including or with an electrical insulation" can be understood in that an insulated or coated wire as such is provided.

A ring electrode surrounding the wire can be understood in that the ring electrode at least partially or completely surrounds the wire or covers a circumference ring of the wire at least partially or completely.

In an example, the electrical connecting of the ring electrodes with the wires is a welding, gluing, crimping or the like. A wall thickness of such ring electrode can be in the range of 10 to 200 µm and in one embodiment 20 to 50 µm. The ring electrodes can have various shapes and are in one embodiment round or angular with or without rounded corners.

In an example, the manufacturing method for a microlead further includes a bundling of the first and second wires by means of a sub-sheath surrounding the wires.

In an example, the bundling is a heating of the sheath. The first and/or second and/or the sub-sheath can be a heat shrink.

In an example, the partial removing of the first and the second sheath from the ring electrodes is a laser ablation, a mechanical cutting or the like. The ring electrode portions can be understood as sub-electrodes or windows. A number of ring electrode portions can be in the range of 1 to 300 and in one embodiment 1 to 36. The ring electrode portions can have various shapes and are in one embodiment angular. The ring electrode portions can be at least partially arranged axially above each other, but also all other arrangements are possible. The high number of ring electrode portions and the various possible shapes allow a very efficient therapy.

The microlead may be manufactured in various configurations, as for example with a larger number of ring electrodes components and/or a larger number of wires:

In an example, the manufacturing method for a microlead further includes a providing of third and a fourth ring electrode component.

In an example, the manufacturing method for a microlead further includes
- a providing of a third and a fourth electrically conductive wire including an electrical insulation,
- providing of a third and a fourth ring electrode around the wires, and
- electrically connecting the third ring electrode with the third wire and the fourth ring electrode with the fourth wire.

In an example, the manufacturing method for a microlead further includes
- providing of a fifth and a sixth electrically conductive wire with an electrical insulation,
- providing of a fifth and a sixth ring electrode around the wires, and
- electrically connecting the fifth ring electrode with the fifth wire and the sixth ring electrode with the sixth wire.

According to one embodiment, also a microlead is presented. The microlead includes:
- a first electrically conductive wire surrounded by an electrical insulation,
- a second electrically conductive wire surrounded by an electrical insulation,
- a first and a second ring electrode surrounding the wires, wherein the first ring electrode is electrically connected with the first wire and the second ring electrode is electrically connected with the second wire,
- a first sheath surrounding the ring electrodes and the wires to obtain a first ring electrode component,
- a second ring electrode component, and
- a second sheath surrounding the ring electrode components, wherein the first and the second sheaths are partially removed from the ring electrodes to expose ring electrode portions.

The present microlead is less complex to be manufactured and therefore cheaper. Additionally, the present microlead can be provided with improved properties. A ratio between an exposed surface of a single ring electrode portion and the microlead's circumference can be very high, which means between 8 and 30% of the individual electrode. A high number of exposed ring electrode portions can be simultaneously combined with a small diameter, for example, 2 to 36 exposed ring electrode portions can be arranged around a circumference of the microlead of less or equal to 1 mm.

In an example, a number of wires within the first sheath is between 1 and 100 and in one embodiment between 1 and 50.

A diameter of the first and/or the second wire may be in a range of 15 to 250 µm and in one embodiment in a range of 20 to 120 µm.

A number of wires per bundle including the wires, the ring electrodes and the first sheath may be in a range of 2 to 100 and in one embodiment in a range of 2 to 50.

A number of such bundles per microlead may be in the range of 2 to 50 and in one embodiment in a range of 2 to 19.

In an example, the first and/or the second wire include at least two electrically conductive sub-wires.

In an example, a diameter of the microlead is in a range between 0.5 and 1.5 mm and the microlead further includes several ring electrode components and between 2 and 36 exposed ring electrode portions and in one embodiment between 12 and 36 exposed ring electrode portions.

The exposed ring electrode portions may cover between 1 and 50% of the microlead's circumference, in one embodiment between 5 and 30%, in one embodiment between 8 and 25% or between 15 and 30%. One of the exposed ring electrode portions may have a surface between 0.01 and 5 mm$^2$ and in one embodiment between 0.01 and 2 mm$^2$.

The microlead may have various configurations, as for example:
- 4×4, which means four ring electrodes with each having four exposed ring electrode portions, which sum up to 16 sub-electrodes. Each exposed ring electrode portion may then cover between 10 and 25% of the microlead's circumference.
- 5×4, which means five ring electrodes with each having four exposed ring electrode portions, which sum up to 20 sub-electrodes. Each exposed ring electrode portion may then cover between 10 and 25% of the microlead's circumference.

6×4, which means six ring electrodes with each having four exposed ring electrode portions, which sum up to 24 sub-electrodes. Each exposed ring electrode portion may then cover between 10 and 25% of the microlead's circumference.

All wires and sub-wires may include or may be Pt, Ir, Ta, Pd, Ti, Fe, Au, Mo, Nb, W, Ni, Ti and/or the like. All wires and sub-wires may include or may be MP35, 316L, 301, 304 and/or the like. All insulations may include or may be fluoropolymer, polyimide, polyurethane and/or the like. All sheaths and sub-sheats may include or may be PET and/or the like. All ring electrodes may include or may be Pt, Ir, Ta, Pd, Ti, Fe, Au, Mo, Nb, W, Ni, Ti, MP35, 316L, 301, 304 and/or the like.

According to one embodiment, also a microlead system is presented. The microlead system includes a microlead as described above and a pulse generator configured to control the microlead.

According to one embodiment, also a use of a microlead or a microlead system as described above for a pacemaker or a neuromodulator is presented.

It shall be understood that the manufacturing method for a microlead, the microlead, the microlead system including such microlead and the use of such microlead or microlead system according to the independent claims have similar and/or identical in one embodiment, for example, as defined in the dependent claims. It shall be understood further that in one embodiment of the invention can also be any combination of the dependent claims with the respective independent claim.

These and other aspects of one embodiment will become apparent from and be elucidated with reference to the embodiments described hereinafter.

Figure 1B:
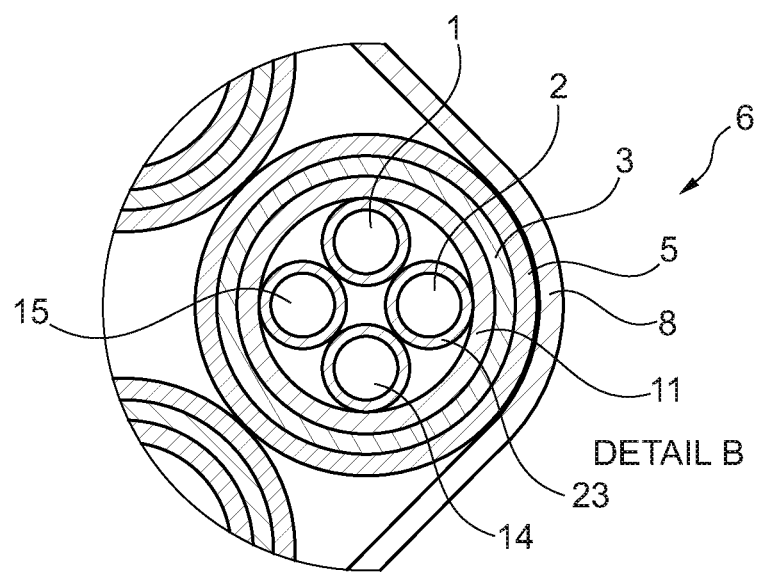
Figure 1C:
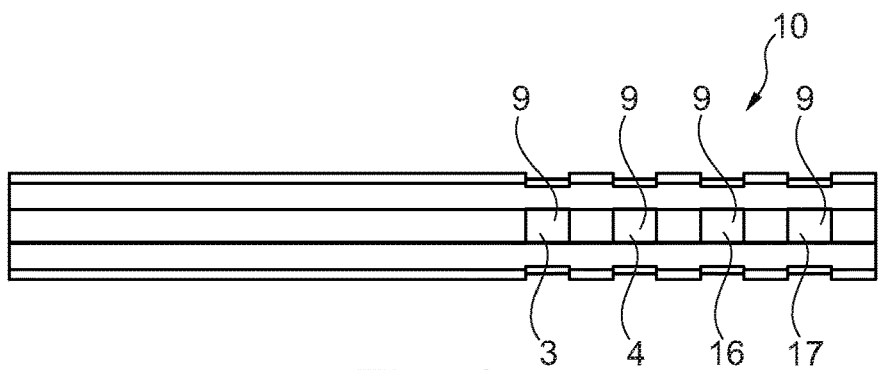

FIGS. 1a)-1c) illustrate schematically and exemplarily a cross-section of a microlead 10 according to the invention in FIG. 1a), a detail view of one part of the microlead 10 in FIG. 1b) and a side view of the microlead 10 in FIG. 1c). The microlead 10 includes a first ring electrode component 6, a second ring electrode component 7, a third ring electrode component 12 and a forth ring electrode component 13. All four ring electrode components 6, 7, 12, 13 are surrounded by a second sheath 8.

Each ring electrode component includes a first wire 1, a second wire 2, a third wire 14 and a forth wire 15. Each wire 1, 2, 14, 15 is surrounded by an electrical insulation 23. Each compound of four wires is surrounded by an optional sub-sheath 11. Each compound of four wires is surrounded by a ring electrode 3. One of the four wires is electrically connected to the ring electrode 3. The other wires are electrically connected to other ring electrodes 4, 16, 17, which are only visible in FIG. 1c). Each compound of wires and ring electrode is surrounded by a first sheath 5 to obtain a ring electrode component 6.

As already said, there are four ring electrode components 6, 7, 12, 13 and all of them together are surrounded by the second sheath 8. The sub-sheath 11, the first sheath 5 and the second sheath 8 are partially removed from the ring electrodes 3, 4, 16, 17 to expose ring electrode portions 9 for an electrically conductive connection with the environment. These exposed ring electrode portions 9 are only visible in FIG. 1c).

Figure 2A:
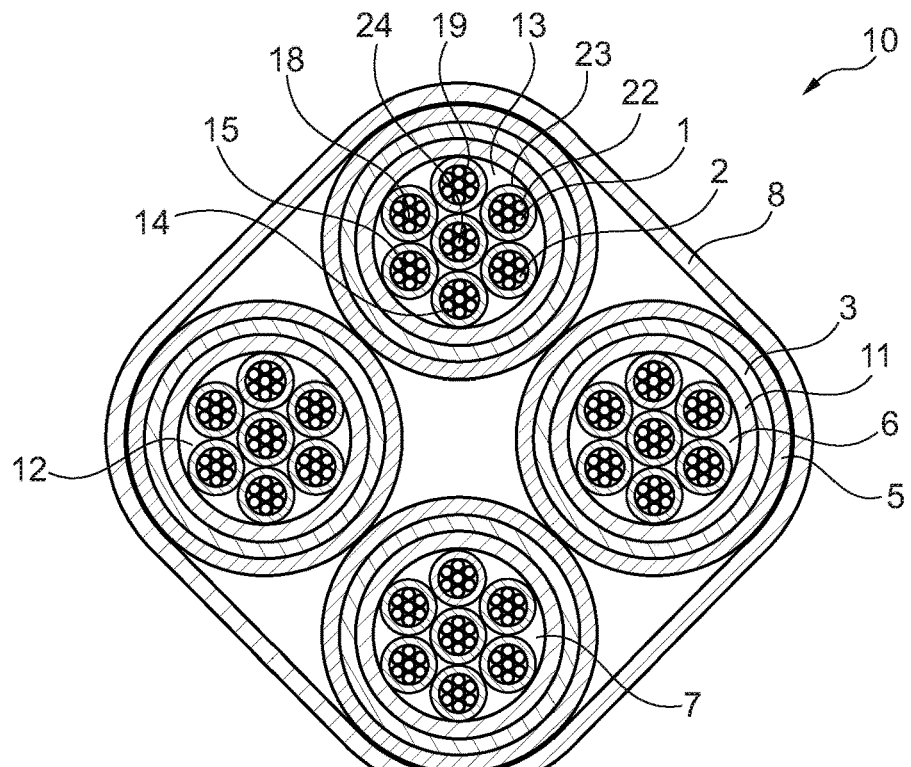
FIGS. 2a-2b illustrate schematically and exemplarily a cross-section of another microlead according to one embodiment in FIG. 2a) and a side view of the microlead in FIG. 2b)
Figure 2B:
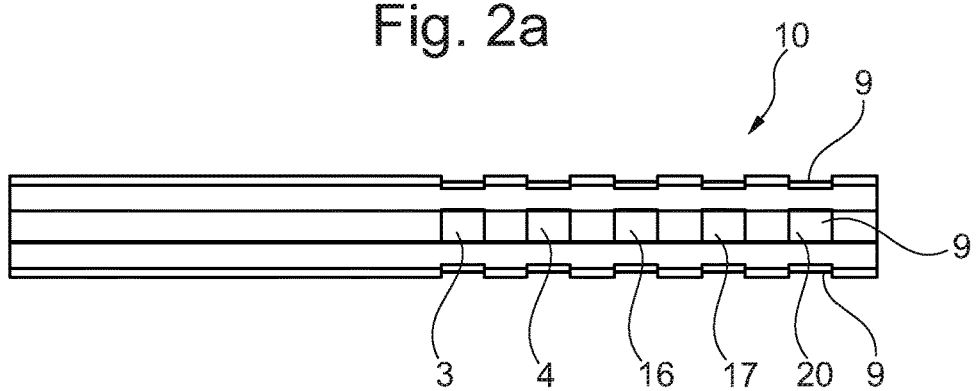

FIGS. 2a)-2b) illustrate schematically and exemplarily a cross-section of another microlead 10 according to the invention in FIG. 2a) and a side view of the microlead 10 in FIG. 2b). The microlead 10 includes again a first ring electrode component 6, a second ring electrode component 7, a third ring electrode component 12 and a forth ring electrode component 13. All four ring electrode components 6, 7, 12, 13 are surrounded by a second sheath 8.

Each ring electrode component includes seven wires, namely a first wire 1, a second wire 2, a third wire 14, a forth wire 15, a fifth wire 18, a sixth wire 19 and a seventh wire 24. Each wire includes seven sub-wires 22. Each wire is surrounded by an electrical insulation 23.

Each compound of seven wires is surrounded by an optional sub-sheath 11 and a ring electrode. All wires are electrically connected to different ring electrodes 3, 4, 16, 17, 20. Each compound of wires and ring electrode is surrounded by a first sheath 5 to obtain a ring electrode component 6.

All four ring electrode components 6, 7, 12, 13 are surrounded by the second sheath 8. The sub-sheath 11, the first sheath 5 and the second sheath 8 are partially removed from the ring electrodes 3, 4, 16, 17, 20 to expose ring electrode portions 9 for an electrically conductive connection with for example tissue. These exposes ring electrode portions 9 are only visible in FIG. 2b).

Figure 3:
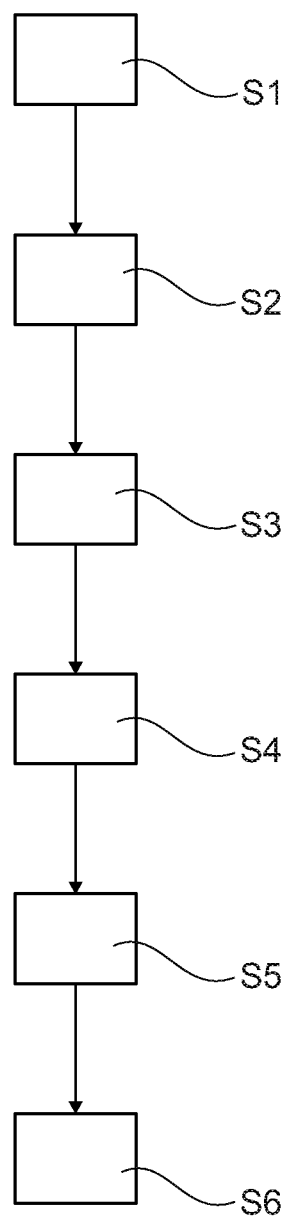
FIG. 3 illustrates a schematic overview of steps of a manufacturing method for a microlead according to one embodiment.

FIG. 3 illustrates a schematic overview of steps of a manufacturing method for a microlead 10 according to the invention. The method includes the following steps:

In a first step S1, providing at least a first electrically conductive wire 1 with an electrical insulation and a second electrically conductive wire 2 with an electrical insulation. The electrical insulation of the wires 1, 2 is a coating around the electrically conductive wire.

In a second step S2, providing a first and a second ring electrode 3, 4 surrounding the wires 1, 2. The ring electrodes 3, 4 are here round.

In a third step S3, electrically connecting the first ring electrode 3 with the first wire 1 and the second ring electrode 4 with the second wire 2. The electrical connecting of the ring electrodes 3, 4 with the wires 1, 2 is a welding, gluing, crimping or the like.

In a fourth step S4, bundling the ring electrodes 3, 4 and the wires 1, 2 by means of a first sheath 5 surrounding the ring electrodes 3, 4 and the wires 1, 2 to obtain a first ring electrode component 6. The bundling is a heating of the first sheath 5, which is a heat shrink.

In a fifth step S5, providing a second ring electrode component 7.

In a sixth step S6, bundling the ring electrode components 6, 7 by means of a second sheath 8 surrounding the ring electrode components 6, 7. The bundling is a heating of the second sheath 8, which is a heat shrink.

In a seventh step S7, partially removing the first and the second sheaths 5, 8 from the ring electrodes 3, 4 to expose ring electrode portions 9. The partial removing of the first and the second sheath 5, 8 from the ring electrodes 3, 4 is a laser ablation, a mechanical cutting or the like. The ring electrode portions 9 are here angular and they are arranged axially above each other.

The present manufacturing method for a microlead is less complex than conventional manufacturing methods and provides microleads, which are more reliable and for example, more corrosion resistant than microleads manufactured according to conventional (thin film) manufacturing methods. Further, the present manufacturing method is very flexible and allows manufacturing various shapes and sizes of ring electrodes and exposed ring electrode portions.

A microlead can be manufactured, which is very small, for example, with respect to its diameter to avoid injuries of a venous, arterial, or lymphatic network, in which it is to be inserted. The diameter of a microlead manufactured according to the present manufacturing method can be below or equal to 1.2 mm and in one embodiment below or equal to 1 mm.

The present manufacturing method allows manufacturing such small microleads with still a high number of electrodes and/or exposed electrode portions as for example up to 36 exposed electrode portions. The electrodes and/or the exposed electrode portions may still have large electrode surfaces, which allow using less current densities, which again avoid injuries of the venous, arterial, or lymphatic network.

It has to be noted that embodiments of the invention are described with reference to different subject matters. For example, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A manufacturing method for a microlead, comprising:
   providing at least an electrically conductive first wire having an electrical insulation and an electrically conductive second wire having an electrical insulation,
   providing a first ring electrode and a second ring electrode at least partially surrounding the first and second wires,
   electrically connecting the first ring electrode with the first wire and the second ring electrode with the second wire,
   bundling the first and second ring electrodes and the first and second wires by means of a first sheath at least partially surrounding the first and second ring electrodes and the first and second wires to obtain a first ring electrode component,
   providing a second ring electrode component in a fashion similar to providing the first ring electrode component,
   bundling the first and second ring electrode components by means of a second sheath at least partially surrounding the first and second ring electrode components, and
   partially removing the first and the second sheaths to expose ring electrode portions of the first and second ring electrode components, wherein the exposed ring electrode portions cover between 8 and 25% of the circumference of the microlead.

2. The manufacturing method of claim 1, wherein the bundling is a heating of the first or second sheath, which is a heat shrink.

3. The manufacturing method of claim 1, wherein the electrical insulation of the wires is a coating around the electrically conductive wire.

4. The manufacturing method of claim 1, wherein the electrical connecting of the ring electrodes with the wires is a welding, gluing or crimping.

5. The manufacturing method of claim 1, wherein the partial removing of the first and the second sheath from the ring electrodes is a laser ablation or a mechanical cutting.

6. The manufacturing method of claim 1, further comprising a bundling of the first and second wires by means of a sub-sheath surrounding the wires.

7. The manufacturing method of claim 1, further comprising a providing of third ring electrode component and a fourth ring electrode component.

8. The manufacturing method of claim 1, further comprising:
   providing of a third electrically conductive wire comprising an electrical insulation and a fourth electrically conductive wire comprising an electrical insulation,
   providing of a third ring electrode and a fourth ring electrode around the wires, and
   electrically connecting the third ring electrode with the third wire and the fourth ring electrode with the fourth wire.

9. A microlead, comprising:
   an electrically conductive first wire having an electrical insulation,
   an electrically conductive second wire comprising an electrical insulation,
   a first ring electrode and a second ring electrode at least partially surrounding the first and second wires, wherein the first ring electrode is electrically connected with the first wire and the second ring electrode is electrically connected with the second wire,
   a first sheath at least partially surrounding the first and second ring electrodes and the first and second wires to obtain a first ring electrode component,
   a second ring electrode component having a structure the same as that of the first ring electrode component, and
   a second sheath at least partially surrounding the first and second ring electrode components, wherein the first and the second sheaths are partially removed to expose ring electrode portions of the first and second ring electrode components, wherein the exposed ring electrode portions cover between 8 and 25% of the circumference of the microlead.

10. The microlead of claim 9, wherein the first and/or the second wire comprise at least two electrically conductive sub-wires.

11. The microlead of claim 9, wherein a diameter of the microlead is in a range between 0.5 and 1.5 mm and the microlead further comprises several ring electrode components and between 12 and 36 exposed ring electrode portions.

12. The microlead of claim 9, wherein a number of wires within the first sheath is between 1 and 50.

13. The microlead of claim 9 incorporated in a microlead system further comprising a pulse generator configured to control the microlead.

14. The microlead of claim 9 used as a pacemaker or a neuromodulator.

15. The method of claim 1, wherein the exposed ring electrode portions cover between 10 and 25% of the circumference of the microlead.

* * * * *